(12) United States Patent
Sen

(10) Patent No.: US 8,248,050 B2
(45) Date of Patent: Aug. 21, 2012

(54) MULTI-CHANNEL LOW VOLTAGE MICRO-ELECTRIC-FIELD GENERATOR

(75) Inventor: Luyi Sen, Shanghai (CN)

(73) Assignee: Suntek Medical Scientific and Technologies (Shanghai) Co., Ltd., Shanghai (CN)

( * ) Notice: Subject to any disclaimer, the term of this patent is extended or adjusted under 35 U.S.C. 154(b) by 0 days.

(21) Appl. No.: 12/915,080

(22) Filed: Oct. 29, 2010

(65) Prior Publication Data

US 2011/0101945 A1 May 5, 2011

Related U.S. Application Data

(63) Continuation of application No. PCT/CN2008/001022, filed on May 26, 2008.

(30) Foreign Application Priority Data

Apr. 29, 2008 (CN) .......................... 2008 1 0036767

(51) Int. Cl.
| | |
|---|---|
| G05F 1/56 | (2006.01) |
| G05F 1/563 | (2006.01) |
| G05F 1/565 | (2006.01) |
| G05F 1/569 | (2006.01) |
| G05F 1/575 | (2006.01) |
| G05F 1/62 | (2006.01) |

(52) U.S. Cl. ......... 323/282; 323/285; 323/266; 323/276

(58) Field of Classification Search .................. 323/241, 323/266, 268–276, 282–286
See application file for complete search history.

(56) References Cited

U.S. PATENT DOCUMENTS

| | | | |
|---|---|---|---|
| 6,768,228 B1* | 7/2004 | Fial et al. ...................... | 307/131 |
| 6,912,139 B2* | 6/2005 | Kernahan et al. ............... | 363/41 |
| 7,061,215 B2* | 6/2006 | Harris ........................... | 323/268 |
| 7,215,102 B2* | 5/2007 | Harris et al. ................... | 323/268 |
| 2007/0139024 A1* | 6/2007 | Zolfaghari .................... | 323/273 |

* cited by examiner

Primary Examiner — Matthew Nguyen
Assistant Examiner — Nusrat Quddus
(74) Attorney, Agent, or Firm — Matthias Scholl P.C.; Matthias Scholl

(57) ABSTRACT

A biologic and medical multi-channel low voltage micro-electric-field generator including a power supply unit, at least one micro-electric-field generating unit set comprising a step-down unit, a linear regulator unit, and a pulse generating and outputting unit, and a programmable logic control unit. The micro-electric-field generating unit set is connected to an output end of the power supply unit. The step-down unit depresses the voltage of frequency power. The linear regulator unit regulates the output of the step-down unit. The pulse generating and outputting unit turns on/off the output of the linear regulator unit and connects to a network electrode group. The programmable logic control unit controls the characteristics of the output pulse from the pulse generating and outputting unit. The generator is applicable in gene, protein, drug and/or a variety of plasmids delivery to the organs, cells within the tissues of large animal or human.

20 Claims, 5 Drawing Sheets

US 8,248,050 B2

MULTI-CHANNEL LOW VOLTAGE MICRO-ELECTRIC-FIELD GENERATOR

CROSS-REFERENCE TO RELATED APPLICATIONS

This application is a continuation of International Patent Application No. PCT/CN2008/001022 with an international filing date of May 26, 2008, designating the United States, now pending, and further claims priority benefits to Chinese Patent Application No. 200810036767.4 filed Apr. 29, 2008. The contents of all of the aforementioned applications, including any intervening amendments thereto, are incorporated herein by reference.

BACKGROUND OF THE INVENTION

1. Field of the Invention

The invention relates to a biology or medical device, and more particularly to a biologic and medical multi-channel low voltage micro-electric-field generator which is adapted for delivering drugs or mediums in bodies.

2. Description of the Related Art

For more than two decades, electroporation has been the most efficient technique for the delivery of molecules into cells. Electroporation involves the application of short duration and high intensity electric field pulses to cells or tissues. Electric field strength in the order of 1-1.5 kV/cm for duration of a few μs to a few ms are required to cause transient membrane destabilization, then formation of nanometer-sized pores that allow passage of DNA and other macromolecules into the isolated cells. Accordingly, at least several kV might need for electroporation of an entire organ of large animals or humans.

However, existing electric pulses with high electric field intensity cause permanent cell membrane breakdown (cell lysis). Further, electroporation produces a large amount of heat on the target region. All of these restrict the application of electroporation.

Most recently, a system for low strength electric field-mediated in vivo gene, protein and drug delivery in organ and tissue of large animal and human has been disclosed. The system delivers drugs, genes, siRNAs, shRNAs, proteins, peptides, antibodies or other biomedical and therapeutic molecules and reagents in skin, soft tissue and bone in vivo and in vitro using low strength electric field networking (LSEFN), which applies for a long time short pulse duration and pulse bursts to cells for membrane permeabilization.

The mechanism and nature of the bioelectric application of LSEFN is appreciated as being qualitatively different than the existing electroporation technologies. The intracellular delivery of drugs and a variety of plasmids in cells or tissue in vitro or in vivo using LSEFN can be systemically infused or injected in a variety of organs or tissue for therapeutic purposes.

However, in the prior art, there is no existing type of multichannel micro electric field generator that is applicable for this technology.

SUMMARY OF THE INVENTION

In view of the above-described problems, it is one objective of the invention to provide a biologic and medical multi-channel low voltage micro electric field generator that can be used for in vitro and in vivo intracellular delivery of gene, protein, drug and/or a variety of plasmids in cells of tissues and organs of a large animal or human using low strength electric field networking.

To achieve the above objective, in accordance with one embodiment of the invention, there is provided a biologic and medical multi-channel low voltage micro-electric-field generator, comprising a power supply unit, at least one micro-electric-field generating unit set comprising a step-down unit, a linear regulator unit, and a pulse generating and outputting unit, and a programmable logic control unit; wherein the micro-electric-field generating unit set is connected to an output end of the power supply unit and controlled by the programmable logic control unit; the step-down unit depresses the voltage of frequency power; the linear regulator unit regulates the output of the step-down unit; the pulse generating and outputting unit turns on/off the output of the linear regulator unit rapidly and periodically, forming a pulse output, and switches the voltage range of an output pulse of the linear regulator unit; the programmable logic control unit controls the characteristics of the output pulse from the pulse generating and outputting unit according to preset values and program procedures; and the pulse generating and outputting unit connects to a network electrode group.

In a class of this embodiment, an excess voltage protection unit is disposed at an output end of the linear regulator unit. An input end of the excess voltage protection unit connects to the output end of the linear regulator unit. An output end of the excess voltage protection unit connects to an interrupt port of the programmable logic control unit.

In a class of this embodiment, an excess current protection unit is disposed at an output end of the pulse generating and outputting unit. An input end of the excess current protection unit connects to the output end of the pulse generating and outputting unit. An output end of the excess current protection unit connects to the interrupt port of the programmable logic control unit.

When the excess voltage/current protection unit generates an excess-valued voltage/current signal, the programming logic control unit stops the pulse output of the pulse generating and outputting unit to protect the corresponding unit.

In a class of this embodiment, an optoelectronic isolator is disposed between the excess voltage/current protection unit and the programmable logic control unit. Through the optoelectronic isolator, the excess voltage/current protection unit connects respectively to the interrupt port of the programmable logic control unit.

In a class of this embodiment, the characteristics of the output pulse comprise at least the amplitude, width, interval, frequency thereof, the number of the output pulses in each pulse group (or the length of time of each pulse group), the time interval between two pulse cluster groups (or the repetition rate of each pulse cluster group), and the total time of multiple output pulse cluster groups. Through the program/parameter setting, the programmable logic control unit is capable of setting and adjusting these parameters respectively.

In a class of this embodiment, the programmable logic control unit comprises a single chip micyoco (SCM), a microcontroller, a CPLD/FPGA programmable logic circuit or an embedded processor.

In a class of this embodiment, the pulse generating and outputting unit comprises at least an electronic switching circuit and a voltage level shifting circuit, both controlled by the programmable logic control unit. The electronic switching circuit turns on/off the output of the linear regulator unit rapidly and periodically, forming the required pulse output under the control of the programmable logic control unit. The voltage level shifting circuit pastes/cuts the resistor divider/ shunt resistor at the output end of the linear regulator unit, switching the voltage range of the output pulse under the control of the programmable logic control unit.

In a class of this embodiment, the linear regulator unit is a conventional linear voltage regulator circuit or a low dropout linear voltage regulator circuit.

In a class of this embodiment, the step-down unit is a conventional AC/AC step-down circuit or an AC/DC step-down circuit.

In a class of this embodiment, the excess voltage protection unit is a voltage comparator circuit. The comparator circuit compares the voltage signal from the output end of the linear regulator unit with the preset voltage value. When the value of the voltage exceeds the preset voltage value, the comparator circuit is driven to turn and generates a trigger signal to the interrupt port of the programmable logic control unit. The programmable logic control unit stops the pulse output of the pulse generating and outputting unit to protect the unit.

In a class of this embodiment, the excess current protection unit is a voltage/current comparator circuit comprising a comparator. After the voltage-to-current signal conversion, the comparator compares the current signal from the output end of the pulse generating and outputting unit with the preset current value. When the value of the current exceeds the preset current value, the comparator circuit is driven to turn and generates a trigger signals to the interrupt port of the programmable logic control unit. The programmable logic control unit stops the pulse output of the pulse generating and outputting unit to protect the unit.

In a class of this embodiment, the multichannel low voltage micro electric field generator comprises a plurality of the micro-electric-field generating unit sets and one programmable logic control unit. Each micro-electric-field generating unit set comprises the linear regulator unit and the pulse generating and outputting unit. The programmable logic control unit connects to all the pulse generating and outputting units in all micro-electric-field generating units in a one-to-many method. All the pulse generating and outputting units controlled by the programmable logic control unit, together with the network electrode group, forms a single electric field networking.

In a class of this embodiment, the multichannel low voltage micro electric field generator comprises a plurality of the micro-electric-field generating unit sets and the same number of the programmable logic control units. Each micro-electric-field generating unit set comprises the linear regulator unit and the pulse generating and outputting unit. Each programmable logic control unit connects to one pulse generating and outputting unit in one micro-electric-field generating unit in a one-to-one method. Each pulse generating and outputting unit controlled by its corresponding programmable logic control unit, together with a plurality of network electrode groups, outputs in a controllable multichannel way and forms a complex electric field networking.

In accordance with another embodiment of the invention, there provided is a work process flow for a biologic and medical multi-channel low voltage micro electric field generator, comprising the steps of:
   a) depressing a power supply voltage to below 150 V;
   b) linearly regulating the output of a step-down voltage;
   c) turning on/off the output of a regulated voltage rapidly and periodically using an electronic switching circuit controlled by a programmable logic control unit so as to form a continuous pulse output whose characteristics is controlled by the programmable logic control unit, or a series of multi-pulse cluster group output comprising a plurality of continuous pulse outputs with time intervals between each other; and
   d) combining the pulse output with one or more network electrode groups to form a single or complex electric filed networking.

In a class of this embodiment, the work process flow further comprises detecting the regulated voltage; the regulated voltage is compared with a preset voltage value and the programmable logic control unit receives the comparison and controls the linear regulator unit to prevent an excess voltage.

In a class of this embodiment, the work process flow further comprises detecting a current signal from the output of the electronic switching circuit; the current signal is compared with a preset current value and the programmable logic control unit receives the comparison and controls the electronic switching circuit to prevent an excess current.

In a class of this embodiment, the output pulse signal is a pulse signal of several ten of volts, volts, millvolts, or microvolts.

In a class of this embodiment, the frequency level of the rapid and periodical turning on/off is Hertz-level.

In a class of this embodiment, the characteristics of the output pulse comprise at least the amplitude, width, interval and frequency thereof, the number of output pulses in each pulse group or the length of time of each pulse group, the time interval between two pulse cluster groups or the repetition rate of each pulse cluster group, and the total time of multiple output pulse cluster groups. Through the program/parameter setting, the programmable logic control unit is capable of setting and adjusting these parameters respectively.

The definitions of the low strength electric field networking, network electrode group, pulse cluster group, and time interval between two pulse cluster groups of the invention are the same as that disclosed by the prior art.

Advantages of the invention are summarized below:
1. The step-down unit significantly depresses the output pulse voltage and the linear regulator unit regulates the amplitude, which completely fulfill the application requirement of low strength electric field networking;
2. The programmable logic control unit is capable of adjusting each characteristic of the output pulse at any time as required, which is more applicable for the need of medical research, experiment, and therapy;
3. Excess voltage/current protection units make the application more safe and reliable, which completely fulfill the requirement of medical and clinical use;
4. The programmable logic control unit connects to the pulse generating and outputting units in both one-to-many and one-to-one methods, which is more flexible to control and provides a better introducing effect; and
5. Electronic switching circuit turns on/off the output of the linear regulator unit rapidly and periodically to form the required pulse output, which makes the structure of the whole circuit more simple and practical, and makes the pulse output more stable and reliable.

DETAILED DESCRIPTION OF THE EMBODIMENTS

For further illustrating the invention, experiments detailing a biologic and medical multi-channel low voltage micro-electric-field generator are described below. It should be noted that the following examples are intended to describe and not to limit the invention.

Figure 1:
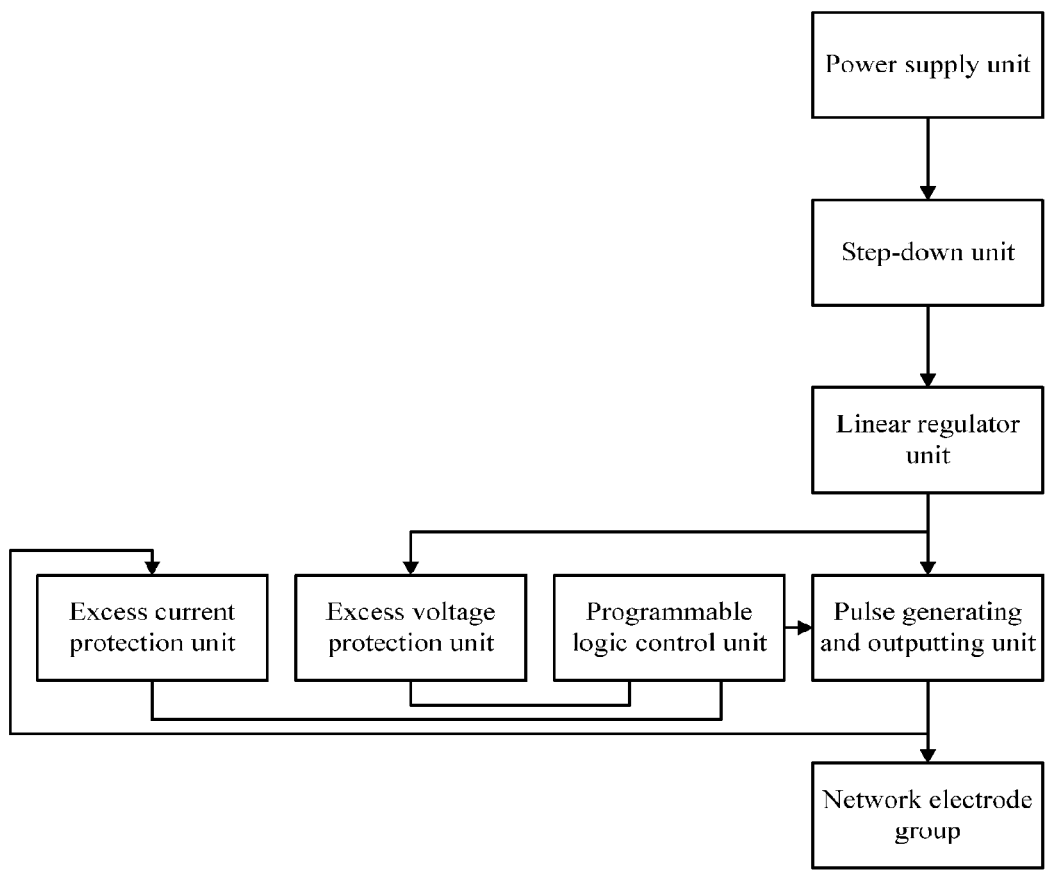
FIG. 1 is a block diagram of a circuit structure of a biologic and medical multi-channel low voltage micro-electric-field generator according to one embodiment of the invention.

As shown in FIG. 1, a biologic and medical multi-channel low voltage micro-electric-field generator, comprises a power supply unit, at least one micro-electric-field generating unit set comprising a step-down unit, a linear regulator unit, and a pulse generating and outputting unit, and a programmable logic control unit. The micro-electric-field generating unit set is connected to an output end of the power supply unit and controlled by the programmable logic control unit. The step-down unit depresses the voltage of frequency power. The linear regulator unit regulates the output of the step-down unit. The pulse generating and outputting unit turns on/off the output of the linear regulator unit rapidly and periodically, forming a pulse output, and switches the voltage range of an output pulse of the linear regulator unit. The programmable logic control unit controls the characteristics of the output pulse from the pulse generating and outputting unit according to preset values and program procedures. The pulse generating and outputting unit connects to one or more network electrode groups.

An excess voltage protection unit is disposed at an output end of the linear regulator unit. An input end of the excess voltage protection unit connects to the output end of the linear regulator unit.

An excess current protection unit is disposed at an output end of the pulse generating and outputting unit. An input end of the excess current protection unit connects to the output end of the pulse generating and outputting unit.

An output of end the excess voltage protection unit and an output end of the excess current protection unit connect to the interrupt ports of the programmable logic control unit.

When the excess voltage/current protection unit generates an excess-valued voltage/current signal, the programming logic control unit stops the pulse output of the pulse generating and outputting unit to protect the corresponding unit.

Furthermore, an optoelectronic isolator is disposed between the excess voltage/current protection unit and the programmable logic control unit. Through the optoelectronic isolator, the excess voltage/current protection unit connects respectively to the interrupt port of the programmable logic control unit.

The characteristics of the output pulse comprise at least the amplitude, width, interval, frequency thereof, the number of the output pulses in each pulse group (or the length of time of each pulse group), the time interval between two pulse cluster groups (or the repetition rate of each pulse cluster group), and the total time of multiple output pulse cluster groups. Through the program/parameter setting, the programmable logic control unit is capable of setting and adjusting these parameters respectively.

The programmable logic control unit comprises a single chip micyoco (SCM), a microcontroller, a CPLD/FPGA programmable logic circuit or an embedded processor.

The pulse generating and outputting unit comprises at least an electronic switching circuit and a voltage level shifting circuit, both controlled by the programmable logic control unit.

The electronic switching circuit turns on/off the output of the linear regulator unit rapidly and periodically, forming the required pulse output under the control of the programmable logic control unit.

The voltage level shifting circuit pastes/cuts the resistor divider/shunt resistor at the output end of the linear regulator unit, switching the voltage range of the output pulse under the control of the programmable logic control unit.

The linear regulator unit can be a conventional linear voltage regulator circuit or a low dropout (LDO) linear voltage regulator circuit.

The step-down unit is a conventional AC/AC step-down circuit or an AC/DC step-down circuit.

The excess voltage protection unit is a voltage comparator circuit. The comparator circuit compares the voltage signal from the output end of the linear regulator unit with the preset voltage value. When the value of the voltage exceeds the preset voltage value, the comparator circuit is driven to turn and generates a trigger signal to the interrupt port of the programmable logic control unit. The programmable logic control unit stops the pulse output of the pulse generating and outputting unit to protect the unit.

The excess current protection unit is a voltage/current comparator circuit comprising a comparator. After the voltage-to-current signal conversion, the comparator compares the current signal from the output end of the pulse generating and outputting unit with the preset current value. When the value of the current exceeds the preset current value, the comparator circuit is driven to turn and generates a trigger signals to the interrupt port of the programmable logic control unit. The programmable logic control unit stops the pulse output of the pulse generating and outputting unit to protect the unit.

The detailed working principle of the excess voltage protection circuit, excess voltage protection circuit, and a typical circuit thereof have been disclosed by the prior art.

Figure 2:
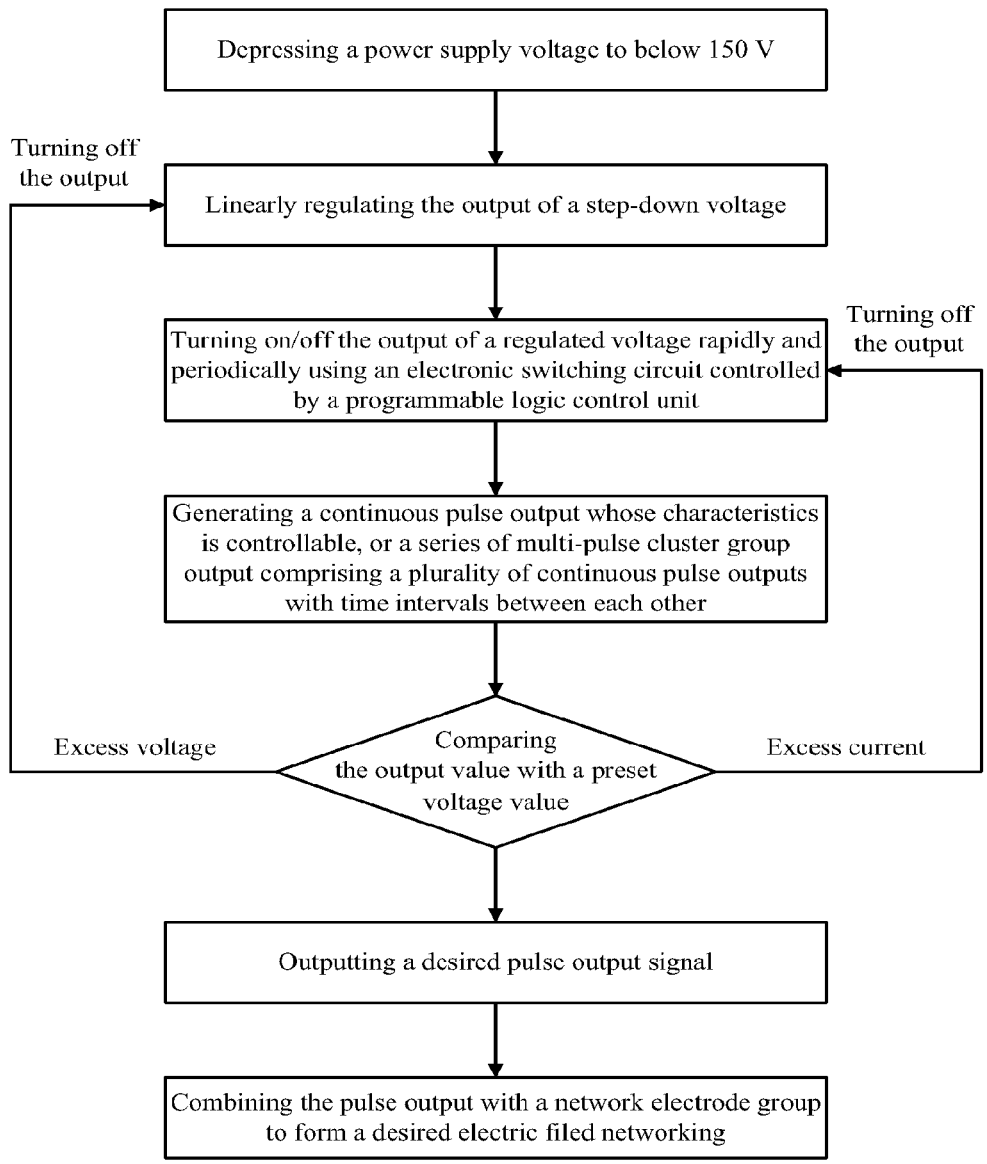
FIG. 2 is a flow chart of a work process of a biologic and medical multi-channel low voltage micro-electric-field generator according to one embodiment of the invention.

As shown in FIG. 2, a work process flow for a biologic and medical multi-channel low voltage micro electric field generator is provided, comprising the steps of:
  a) depressing a power supply voltage to below 150 V;
  b) linearly regulating the output of a step-down voltage;
  c) turning on/off the output of a regulated voltage rapidly and periodically using an electronic switching circuit controlled by a programmable logic control unit so as to form a continuous pulse output whose characteristics is controlled by the programmable logic control unit, or a series of multi-pulse cluster group output comprising a plurality of continuous pulse outputs with time intervals between each other; and
  d) combining the pulse output with one or more network electrode groups to form a single or complex electric filed networking.

The work process flow further comprises detecting the regulated voltage; the regulated voltage is compared with a preset voltage value and the programmable logic control unit receives the comparison and controls the linear regulator unit to prevent an excess voltage.

The work process flow further comprises detecting a current signal from the output of the electronic switching circuit; the current signal is compared with a preset current value and the programmable logic control unit receives the comparison and controls the electronic switching circuit to prevent an excess current.

The output pulse signal is a pulse signal of several ten of volts, volts, millvolts, or microvolts.

The frequency level of the rapid and periodical turning on/off is Hertz-level.

The characteristics of the output pulse comprise at least the amplitude, width, interval and frequency thereof, the number of output pulses in each pulse group or the length of time of each pulse group, the time interval between two pulse cluster groups or the repetition rate of each pulse cluster group, and the total time of multiple output pulse cluster groups. Through the program/parameter setting, the programmable logic control unit is capable of setting and adjusting these parameters respectively.

Figure 3:
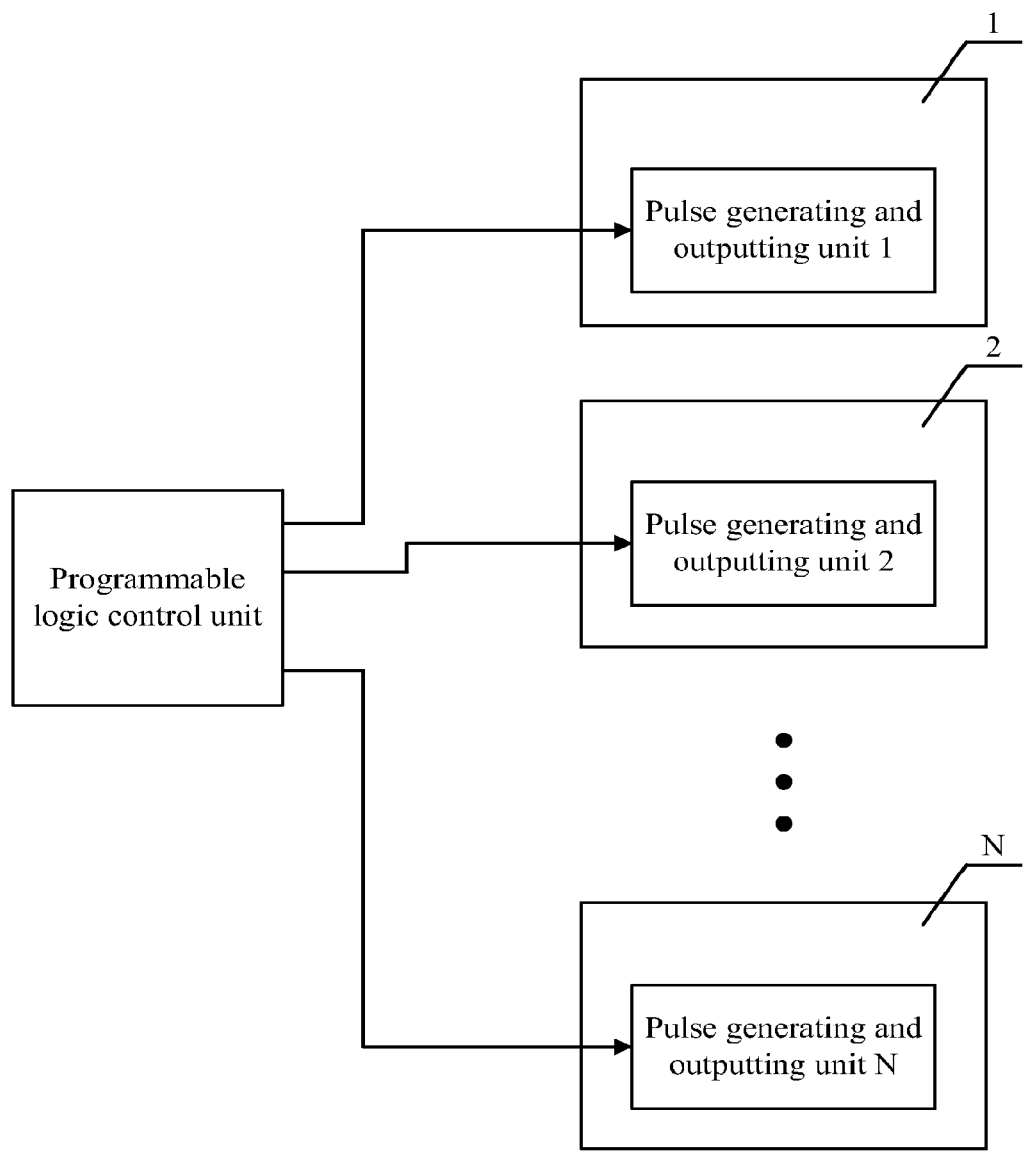
FIG. 3 is a block diagram of a circuit structure of a one-to-many method by which a programmable logic control unit connects to pulse generating and outputting units according to one embodiment of the invention.

As shown in FIG. 3, the multichannel low voltage micro electric field generator comprises a plurality of the micro-electric-field generating unit sets and one programmable logic control unit. Each micro-electric-field generating unit set comprises the linear regulator unit and the pulse generating and outputting unit. The programmable logic control unit connects to all the pulse generating and outputting units in all micro-electric-field generating units in a one-to-many method. All the pulse generating and outputting units controlled by the programmable logic control unit, together with the network electrode group, forms a single electric field networking.

Figure 4:
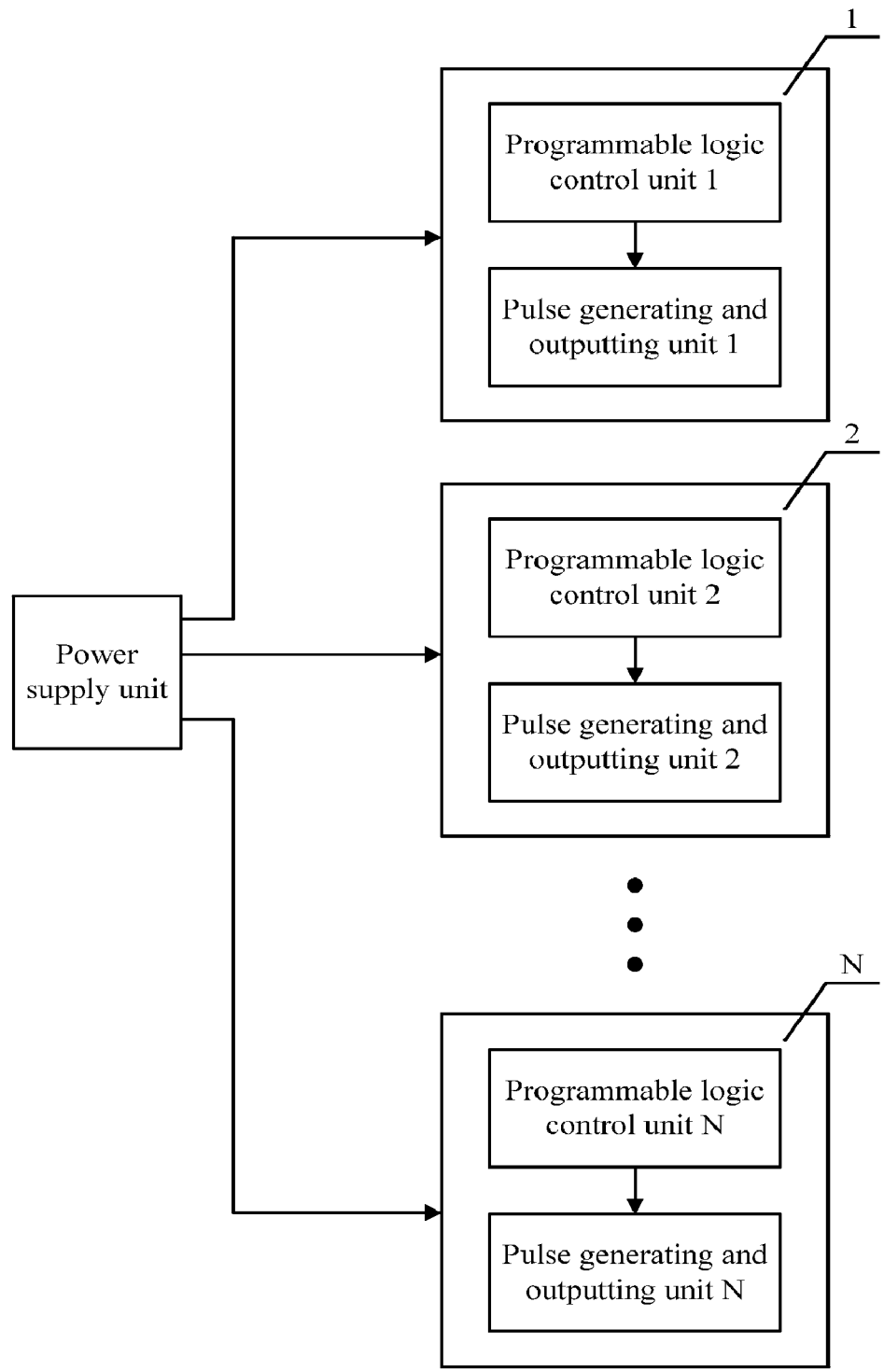
FIG. 4 is a block diagram of a circuit structure of a one-to-one method in which a programmable logic control unit connects to a pulse generating and outputting unit according to one embodiment of the invention.

As shown in FIG. 4, the multichannel low voltage micro electric field generator comprises a plurality of the micro-electric-field generating unit sets and the same number of the programmable logic control units. Each micro-electric-field generating unit set comprises the linear regulator unit and the pulse generating and outputting unit. Each programmable logic control unit connects to one pulse generating and outputting unit in one micro-electric-field generating unit in a one-to-one method. Each pulse generating and outputting unit controlled by its corresponding programmable logic control unit, together with a plurality of network electrode groups, outputs in a controllable multichannel way and forms a complex electric field networking.

The one-to-many method as shown in FIG. 3 and one-to-one method as shown in FIG. 4 generate different low strength electric field networking, thereby forming different overlapping/combination effect of electric field strength/direction to fulfill the requirement of medical and clinical use.

In practical use, the connection types are not confined to the one as shown in FIGS. 3 and 4. To get a better medical treatment effect and to be applicable in different situation, it is possible for a part of micro-electric-field generating units connect to a programmable logic control unit in a many-to-one method, and for another part of micro-electric-generating units connects to the programmable logic control unit in a one-to-one method.

Figure 5:
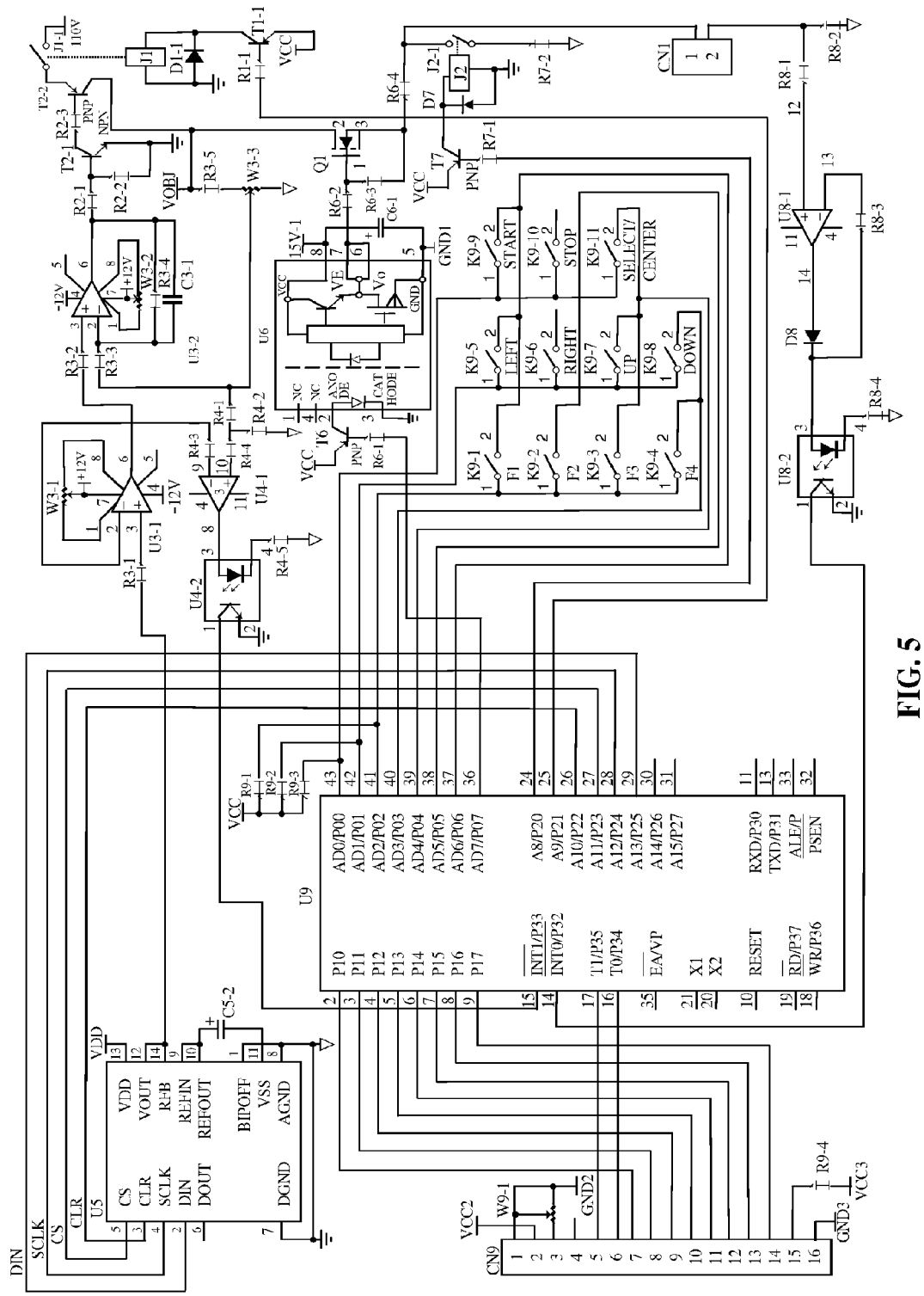
FIG. 5 is an electrical circuit diagram according to one embodiment of the invention, wherein 1-N represents micro-electric-field generating unit sets.

As shown in FIG. 5, an electrical circuit diagram is provided. The power supply unit and the step-down unit are hidden for the concise explanation. In the figure, a relay J1, a triode T1-1, a resistance R1-1, and a diode D1-1 form a power-on circuit. IC op amps U3-1 and U3-2, triodes T2-1 and T2-2, resistances R3-1 to R3-5 and R2-1 to R2-3, adjustable resistances W3-1 to W3-3, and a capacitor C3-1 form a linear regulator circuit. An IC U6, a triode T6, resistances R6-1 to R6-4, a FET Q1, and a capacitor C6-1 form an electronic switching circuit. A triode T7, resistances R7-1 and R7-2, a diode D7, and a relay J2 form a voltage level shifting circuit. An IC U4-1, an optoelectronic isolator U4-2, and resistances R4-1 to R4-5 form an excess voltage protection circuit. An IC U8-1, an optoelectronic isolator U8-2, resistances R8-1 to R8-4, and a diode D8 form an excess current protection circuit. ICs U5 and U9, resistances R9-1 to R9-4, and button switches K9-1 to K9-11 form a programmable logic control circuit.

The diode D1-1 parallel connects to the both ends of the relay J1. One coil end of J1 is terminated to earth ground and the other connects to a collector of the triode T1-1. An emitter of T1-1 connects to a VCC end of the power supply, and through the resistance R1-1, a base of T1-1 connects to A9/P21 pin of the IC U9 in the programmable logic control circuit. The contact J1-1 series connects between 110V power supply and an emitter of the triode T2-2 in the linear regulator circuit.

Through the resistance R3-1, the positive input terminal 3 of the IC U3-1 connects to the RFB pin of the IC U5 in the programmable logic control circuit. Through the resistance R4-3, the negative input terminal 2 of the IC U3-1 connects to the negative input terminal 9 of the IC U4-1 in the excess voltage protection circuit. The terminal 1 and 8 of U3-1 connect to two fixed ends of the adjustable resistance W3-1, and the terminal 7 of U3-1 connects to the free end of W3-1 and +12V power supply. The terminal 4 of U3-1 connects to −12V power supply. Through the resistance R3-2, the terminal 6 of U3-1 connects to the positive input terminal 3 of the IC U3-2. Through the resistance R3-3, the negative input terminal 2 of the IC U3-2 connects to the free end of the adjustable resistance W3-3. The resistance R3-4 and the capacitor C3-1 parallel connects between the negative input terminal 2 and the output terminal 6 of U3-2. The terminal 1 and 8 of U3-2 connect to two fixed end of the adjustable resistance W3-2. Its terminal 7 connects to the free end of W3-2 and +12V power supply. The terminal 4 of U3-2 connects to −12V power supply. Through the resistance R2-1, the terminal 6 connects to the base of the triode T2-1. Through the resistance R2-3, the collector of T2-1 connects to the base of the triode T2-2. The emitter of T2-1 is terminated to earth ground and the resistance R2-2 parallel connects between the base of T2-1 and the earth ground. The collector of T2-2 connects to one end of the resistance R3-5 and the VOBJ end. The other end of R3-5 connects to one fixed end of W3-3. The other fixed end of W3-3 is terminated to signal ground.

Through the resistance R6-1, the AD7/P07 pin of the IC U9 in the programmable logic control circuit connects to the base of the triode T6 in the electronic switching circuit. The emitter of T6 connects to VCC end of the power supply. Its collector connects to the 2 pin (ANODE) of the IC U6. The 3 pin (CATHODE) of U6 is terminated to earth ground, 5 pin (GND) connects to GNDI end, and 8 pin (VCC) connects to 15V-1 end. The capacitor C6-1 parallel connects between the 8 pin and 5 pin. Through the resistance R6-2, the 6 and 7 pin (VE, VO) parallel connects to the 1 pin (G pole) of the FET Q1. The 2 pin (D pole) of Q1 connects to the collector of the triode T2-2 in the linear regulator circuit. Through the resistance R6-4, the 3 pin (S pole) connects to terminal 1 of the output sub-interface CN1. The resistance R603 parallel connects between the 1 pin (G pole) and 3 pin (S pole) of Q1.

Through the resistance R7-1, the A8/P20 pin of the IC U9 in the programmable logic control circuit connects to the base of the triode T7 in the voltage level shifting circuit. The emitter of T7 connects to the VCC end. The collector of T7 connects to one coil end of the relay J2 and the other coil end of J2 is terminated to earth ground. The diode D7 parallel connects between two coil ends of J2. One end of the contact J2-1 of J2 connects to terminal 1 of the output sub-interface CN1, and the other end is terminated to signal ground through the resistance R7-2.

Through the resistance R4-3, the negative input terminal of the IC U3-1 in the linear regulator circuit connects to the negative input terminal of the IC U4-1 in the excess voltage protection circuit. Through the resistance R4-1 and R4-4, the free end of the adjustable resistance W3-3 connects to the positive input terminal of U4-1. The connecting pins of R4-1 and R4-4 are terminated to signal ground through the resistance R4-2. The output terminal of U4-1 connects to the terminal 3 of the optoelectronic isolator U4-2. The terminal 4 of U4-2 is terminated to earth ground through the resistance R4-5. The terminal 2 is terminated to earth ground and terminal 1 connects to the second interrupt port $\overline{INT1}$ of the IC U9 in the programmable logic control circuit.

The terminal 2 of CN1 is terminated to signal ground through the resistance R8-2, and connects to the positive input terminal of the IC U8-1 through the resistance R8-1. The output of U8-1 connects to the terminal 3 of the optoelectronic isolator U8-2 through the diode D8. The resistance R8-3 series connects between the negative input terminal and the terminal 3 of U8-2. The terminal 4 of U8-2 is terminated to signal ground through the resistance R8-4. The terminal 2 is terminated to earth ground and terminal 1 connects to the first interrupt port $\overline{INT0}$ of the IC U9 in the programmable logic control circuit.

The IC U9 in the programmable logic control circuit is a CPU, which is a SCM, a microcontroller, a CPLD/FPGA programmable logic circuit, or an embedded processor. Besides the terminals or pins aforementioned, the I/O ports (AD0/PO0-AD7/PO7 shown in the figure) respectively connect to the resistances R9-1 to R9-3 and the button switches K9-1 to K9-11, thereby forming a switch matrix circuit. The I/O ports (P0-P7 shown in the figure) respectively connect to the terminals of output sub-interface CN9, thereby forming the LCD display circuit. The I/O ports (A10/P22-A13/P25 shown in the figure) respectively connect to the CS, CLR, SCLK and DIN ports of the IC U5, thereby forming a digital/analog signals conversion circuit.

It should be noted that, "terminated to the earth ground" means the ground point connection with the weak current part (Relative to the "Strong current" pulse signal part) of the generator, and "terminated to the signal ground" means the "ground" point connection with the "strong current" part of the pulse signals output. These two terms are different in their ground symbol.

Among the ICs, U3 can be an OP07XX series chip, U4-2 and U8-1 can be LM2XX series chips, U5 can be a MAX53X series chip, U6 can be a HCPL-31XX series chip, U4-1 and U8-2 can be conventional optoelectronic isolators, U9 can be an AT89C51 series chip, and no special requirements for rest components.

Types of the ICs are not confined to the listed types. Any ICs with the same or similar functions are practicable.

The module circuits are not confined to the mentioned circuit in the embodiments. For example, the step-down unit can be an AC/AC, AC/DC, or DC/DC step-down circuit. The power-on circuit can be an electronic switching circuit (such as a silicon controlled circuit). The linear regulator unit can be a conventional linear regulator circuit comprised of OP Amp ICs, or a low dropout linear voltage regulator circuit (for example, AP2XXX series, APE89XX series, TPS7XXX series or UC2XXX series LOD ICs). One or more voltage level shifting circuits are used to switching the voltage range among the several ten of volts, volts, millvolts or microvolts by pasting/cutting the resistor divider/shunt resistor.

Furthermore, from the view of the topological structure of the module circuit, the present generator comprises a plurality of the micro-electric-field generating unit sets and one programmable logic control unit. Each micro-electric-field generating unit set comprises the linear regulator unit and the pulse generating and outputting unit. The programmable logic control unit connects to all the pulse generating and outputting units in each micro-electric-field generating unit in a one-to-many method. All the pulse generating and outputting units controlled by the programmable logic control unit, together with the network electrode group, form an electric field networking.

Optionally, from the view of the topological structure of the module circuit, the generator comprises a plurality of the micro-electric-field generating unit sets and the same number of the programmable logic control units (Only one of the units are shown in this figure). Each micro-electric-field generating unit set comprises the linear regulator unit and the pulse generating and outputting unit. Each programmable logic control unit connects to one pulse generating and outputting unit in one micro-electric-field generating unit in a one-to-one method. Each pulse generating and outputting unit controlled by its corresponding programmable logic control unit, together with multiple network electrode groups, outputs in a controllable multichannel way and forms a complex electric field networking.

The multichannel is the multiple pulse signals with the same or different "characteristics" outputted by multiple network electrodes.

The characteristics of the output pulse comprise at least the amplitude, width, interval and frequency thereof, the number of output pulses in each pulse group (or the length of time of each pulse group), the time interval between two pulse cluster group (or the repetition rate of each pulse cluster group), and the total time of multiple output pulse cluster groups. Through the program/parameter setting, the programmable logic control unit is capable of setting and adjusting these parameters respectively.

In practical use, the parameters are set/adjusted through the switch matrix circuit comprising button switches K9-1 to K9-11. The details of the setting objects of each switch are shown in the figure. All the settings and adjustments have been defined through software design and programming.

The working principle of the generator is described as follow:

In the illustrated examples, when the IC U9 generates a power-on signal, the triode T1-1 breakovers. The coil of the relay J1 picks up and its contact J1-1 turns on 110V power supply. Otherwise, when U9 generates a power-off signal, T1-1 cuts off. The coil of J1 drops out, and the contact J1-1 releases to turn off the power.

The IC U5 in the programmable logic control circuit convert the preset digital signals to analog signals. Through the resistance R3-1, these signals are provided to the IC U3-1 as the reference voltage. Through its negative input terminal and the resistance R4-3, the signals are provided to the IC U4-1 as the reference voltage. The output of U3-1 is provided to the IC U3-2 as the reference voltage.

The triode T2-1 and T2-2 form a compound regulator tube. 110V power supply is regulated by the compound regulator tube to an applicable voltage and then output via T2-2.

Meanwhile, the output voltage is divided by the resistance R3-5 and the adjustable resistance W3-3 and sent to the IC U3-2 via the resistance R3-3 as a voltage to be compared. Furthermore, the output voltage divided by the resistance R3-5 and the adjustable resistance W3-3 is sent to the excess voltage protection circuit via the resistance R4-1 as a detection voltage.

Through the triode T6 and the IC U6, the IC U9 in the programmable logic control unit rapidly and periodically breakovers and cuts off the FET Q1 according to preset values and program procedures, thereby converting the output voltage of the triode T2-2 in the linear regulator circuit to the pulse output signals through the D pole and S pole of Q1. The pulse output signals output to the network electrode group via the resistance R6-4 and output sub-interface CN1.

According to the need of the application or medical treatment, the IC U5 in the programmable logic control circuit outputs the control signals to the triode T7 through the resistance R7-1. T7 breakovers/cuts off to make the coil of the relay J2 picks up/drops out. The contact J2-1 turns on/off to paste/cut off the resistance R7-3, thereby switching the voltage level of the pulse signals.

The output voltage of the triode T2-2's collector in the linear regulator circuit is divided by the resistance R3-5 and the adjustable resistance W3-3 and sent to excess voltage protection circuit via the resistance R4-1 in the excess voltage protection circuit for the voltage comparison. Once the value of the voltage exceeds the preset voltage value outputted by the IC U3-1, the IC U4-1 generates the excess voltage protection signal, isolates it by the optoelectronic isolator U4-1, and sends it to the interrupt port of the IC U5 in the programmable logic control circuit. When U5 receives the interrupt signal, it generates the cutting-off signal under the control of the program. The triode T1-1 cuts off, the coil of the relay J1 drops out, and the contact J1-1 releases and turns off 110V power supply.

Likewise, converted to the voltage signals by the resistance R8-2, the output pulse signals of CN1 is sent via the resistance R8-1 to the IC U8-1 for the voltage comparison. Once the value of the voltage exceeds the preset voltage value, U8-1 generates the excess voltage protection signal, isolates it by the optoelectronic isolator U8-2, and sends it to the interrupt port of U5 in the programmable logic control circuit. Similar to the procedure of excess voltage protection, when U5 receives the interrupt signal, it generates the cutting-off signal under the control of the program. T1-1 cuts off, the coil of J1 drops out, and J1-1 releases and turns off 110V power supply.

Since the micro-processing circuit and digital/analog conversion circuit are existing technologies, the detail principles, circuit structures, and work process are not described herein.

The present invention can be widely used in intracellular delivery of genes, proteins, drugs and a variety of plasmids in cells or tissue in vivo and in vitro in organs and tissue of large animal and human.

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

The invention claimed is:

1. A micro-electric-field generator, comprising:
a) a power supply unit;
b) at least one micro-electric-field generating unit set comprising a step-down unit, a linear regulator unit, and a pulse generating and outputting unit; and
c) a programmable logic control unit;
d) an excess voltage protection unit; and
e) an excess current protection unit;
wherein:
said micro-electric-field generating unit set is connected to an output end of said power supply unit and controlled by said programmable logic control unit;
said step-down unit depresses a voltage of frequency power;
said linear regulator unit regulates an output of said step-down unit;
said pulse generating and outputting unit turns on/off an output of said linear regulator unit rapidly and periodically, forming a pulse output, and switches the voltage range of an output pulse of said linear regulator unit;
said programmable logic control unit controls the characteristics of the output pulse from said pulse generating and outputting unit according to preset values and program procedures;
said pulse generating and outputting unit connects to a network electrode group;
said excess voltage protection unit is disposed at said output end of said linear regulator unit, and an input end of said excess voltage protection unit connects to said output end of said linear regulator unit;
said excess current protection unit is disposed at an output end of said pulse generating and outputting unit, and an input end of said excess current protection unit connects to said output end of said pulse generating and outputting unit;
an output of said excess voltage protection unit and an output of said excess current protection unit connect to an interrupt port of said programmable logic control unit; and
when said excess voltage/current protection unit generates an excess-valued voltage/current signal, said programming logic control unit stops the pulse output of said pulse generating and outputting unit so as to protect a corresponding unit.

2. The generator of claim 1, wherein
an optoelectronic isolator is disposed between said excess voltage/current protection unit and said programmable logic control unit; and
said excess voltage/current protection unit connects respectively to said interrupt port of said programmable logic control unit via said optoelectronic isolator.

3. The generator of claim 1, wherein the characteristics of said output pulse comprise at least the amplitude, width, interval, frequency thereof, the number of the output pulses in each pulse group or the length of time of each pulse group, the time interval between two pulse cluster groups or the repetition rate of each pulse cluster group, and the total time of multiple output pulse cluster groups; through said program/parameter setting, said programmable logic control unit is capable of setting and adjusting these parameters respectively.

4. The generator of claim 1, wherein said programmable logic control unit comprises a single chip micyoco, a microcontroller, a CPLD/FPGA programmable logic circuit, or an embedded processor.

5. The generator of claim 1, wherein
said pulse generating and outputting unit comprises at least an electronic switching circuit and a voltage level shifting circuit, both controlled by said programmable logic control unit;
said electronic switching circuit turns on/off the output of said linear regulator unit rapidly and periodically, forming a required pulse output under the control of said programmable logic control unit; and
said voltage level shifting circuit pastes/cuts a resistor divider/shunt resistor at said output end of said linear regulator unit, switching the voltage range of said output pulse under the control of said programmable logic control unit.

6. The generator of claim 1, wherein said linear regulator unit is a conventional linear voltage regulator circuit or a low dropout linear voltage regulator circuit.

7. The generator of claim 1, wherein said step-down unit is a conventional AC/AC step-down circuit or an AC/DC step-down circuit.

8. The generator of claim 1, wherein
said excess voltage protection unit is a voltage comparator circuit comparing a voltage signal from the output of said linear regulator unit with a preset voltage value; and
when the value of the voltage exceeds said preset voltage value, comparator circuit is driven to turn and generates a trigger signal to the interrupt port of said programmable logic control unit, and said programmable logic control unit stops the pulse output of said pulse generating and outputting unit to protect the unit.

9. The generator of claim 1, wherein
said excess current protection unit is a voltage/current comparator circuit comprising a comparator, after the a voltage-to-current signal conversion, wherein a voltage signal from the output of said linear regulator unit is converted to a current signal, said comparator compares said current signal from said output end of said pulse generating and outputting unit with a preset current value; and
when the value of the current exceeds said preset current value, said comparator circuit is driven to turn and generates a trigger signals to an interrupt port of said programmable logic control unit, and said programmable logic control unit stops the pulse output of said pulse generating and outputting unit to protect the unit.

10. The generator of claim 1, wherein
said micro electric field micro-electric-field generator comprises a plurality of said micro-electric-field generating unit sets and one programmable logic control unit;
each micro-electric-field generating unit set comprises said linear regulator unit and said pulse generating and outputting unit;
said programmable logic control unit connects to all said pulse generating and outputting units in all micro-electric-field generating units in a one-to-many method; and
all said pulse generating and outputting units controlled by said programmable logic control unit, together with said network electrode group, forms a single electric field networking.

11. The generator of claim 1, wherein
said micro-electric-field generator comprises a plurality of said micro-electric-field generating unit sets and said same number of said programmable logic control units;
each micro-electric-field generating unit set comprises said linear regulator unit and said pulse generating and outputting unit;
each programmable logic control unit connects to one pulse generating and outputting unit in one micro-electric-field generating unit in a one-to-one method; and
each pulse generating and outputting unit controlled by its corresponding programmable logic control unit, together with a plurality of network electrode groups, outputs in a controllable multichannel way and forms a complex electric field networking.

12. A method for using the generator of claim 1, comprising the steps of:
a) depressing voltage of the power supply unit to below 150 V;
b) linearly regulating the output of a step-down voltage;
c) turning on/off the output of regulated voltage rapidly and periodically using an electronic switching circuit controlled by a programmable logic control unit so as to form a continuous pulse output whose characteristics is controlled by said programmable logic control unit, or a series of multi-pulse cluster group output comprising a plurality of continuous pulse outputs with time intervals between each other; and
d) combining the pulse output signal with one or more network electrode groups to form a single or complex electric filed networking.

13. The method of claim 12, further comprising detecting said regulated voltage; said regulated voltage is compared with a preset voltage value and said programmable logic control unit receives the comparison and controls said linear regulator unit to prevent an excess voltage.

14. The method of claim 12, further comprising detecting a current signal from the output of said electronic switching circuit; said current signal is compared with a preset current value and said programmable logic control unit receives the comparison and controls said electronic switching circuit to prevent an excess current.

15. The method of claim 12, wherein said output pulse signal is a pulse signal of several tens of volts, volts, millvolts, or microvolts.

16. The method of claim 12, wherein said characteristics of said output pulse comprise at least the amplitude, width, interval and frequency thereof, the number of output pulses in each pulse group or the length of time of each pulse group, the time interval between two pulse cluster groups or the repetition rate of each pulse cluster group, and the total time of multiple output pulse cluster groups; through said program/parameter setting, said programmable logic control unit is capable of setting and adjusting these parameters respectively.

17. The method of claim 12, wherein a frequency level of the rapid and periodical turning on/off is Hertz-level.

18. The generator of claim 1, wherein a frequency level of the rapid and periodical turning on/off is Hertz-level.

19. The generator of claim 1, wherein an output pulse signal is a pulse signal of several tens of volts, volts, millvolts, or microvolts.

20. A micro-electric-field generator, comprising:
a) a power supply unit;
b) at least one micro-electric-field generating unit set comprising a step-down unit, a linear regulator unit, and a pulse generating and outputting unit;
c) a programmable logic control unit; and
d) an excess voltage protection unit;
wherein:
said micro-electric-field generating unit set is connected to an output end of said power supply unit and controlled by said programmable logic control unit;
said step-down unit depresses a voltage of frequency power;
said linear regulator unit regulates an output of said step-down unit;
said pulse generating and outputting unit turns on/off an output of said linear regulator unit rapidly and periodically, forming a pulse output, and switches the voltage range of an output pulse of said linear regulator unit;
said programmable logic control unit controls the characteristics of the output pulse from said pulse generating and outputting unit according to preset values and program procedures;
said pulse generating and outputting unit connects to a network electrode group;
said excess voltage protection unit is disposed at said output end of said linear regulator unit, and an input end of said excess voltage protection unit connects to said output end of said linear regulator unit;
when said excess voltage protection unit generates an excess-valued voltage signal, said programming logic control unit stops the pulse output of said pulse generating and outputting unit so as to protect a corresponding unit.

* * * * *